United States Patent

Hasegawa et al.

Patent Number: 4,746,742
Date of Patent: May 24, 1988

[54] ANALOGS OF NONREDUCING MONOSACCHARIDE MOIETY OF LIPID A

[75] Inventors: Akira Hasegawa; Makoto Kiso, both of Gifu; Kazuyuki Morihara, Osaka, all of Japan

[73] Assignee: Toho Yakuhin Kogyo Kabushiki Kaisha, Osaka, Japan

[21] Appl. No.: 930,361

[22] Filed: Nov. 12, 1986

[30] Foreign Application Priority Data

Nov. 28, 1985 [JP] Japan .............................. 60-268802
Jul. 24, 1986 [JP] Japan .............................. 61-174436
Aug. 11, 1986 [JP] Japan .............................. 61-188215

[51] Int. Cl.$^4$ .............................................. C07H 5/04
[52] U.S. Cl. .............................................. 536/53; 536/117
[58] Field of Search .............................. 536/53, 117

[56] References Cited

FOREIGN PATENT DOCUMENTS 0045590 3/1985 Japan .................................. 536/117

OTHER PUBLICATIONS

Galanos et al., Int. Rev. Biochem., vol. 14, pp. 239-335, 1977.
Lüderitz et al., Naturwissenschaften, vol. 65, pp. 578-585, 1978.

Primary Examiner—J. R. Brown
Assistant Examiner—Peselev, Elli
Attorney, Agent, or Firm—Wenderoth, Lind & Ponack

[57] ABSTRACT

Provided herein is a derivative of 2-deoxy-2-amino-4-O-phophono-D-glucopyranose, which is derived from lipid A, of the formula:

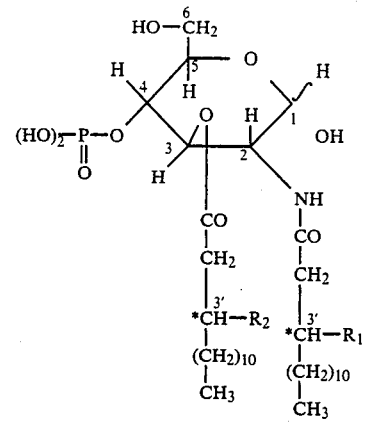

wherein $R_1$ and $R_2$ are a member in a pair selected from the group consisting of those indicated in a following table:

| Compound No. | $R_1$ | $R_2$ |
|---|---|---|
| I(R,R) | —O—CO—$(CH_2)_{12}$—$CH_3$ | —O—CO—$(CH_2)_{12}$—$CH_3$ |
| II | —O—CO—$(CH_2)_{12}$—$CH_3$ | —OH |
| II(R,R) | —O—CO—$(CH_2)_{12}$—$CH_3$ | —OH |
| II(S,S) | —O—CO—$(CH_2)_{12}$—$CH_3$ | —OH |
| III | —OH | —O—CO—$(CH_2)_{12}$—$CH_3$ |
| III(R,R) | —OH | —O—CO—$(CH_2)_{12}$—$CH_3$ |
| III(S,S) | —OH | —O—CO—$(CH_2)_{12}$—$CH_3$ |
| IV(R) | —H | —O—CO—$(CH_2)_{12}$—$CH_3$ |

The compounds of this invention include those of rectus and sinister configurations and act as mitogens for polyclonal B cells.

8 Claims, No Drawings

ANALOGS OF NONREDUCING MONOSACCHARIDE MOIETY OF LIPID A

BACKGROUND OF THE INVENTION (a) Field of the Invention

This invention relates to provide novel analogs of nonreducing monosaccharide subunit of lipid A and stereoisomers thereof. These novel compounds have been synthesized by the present inventors in their course of investigating an effective sugar moiety, which is expected to generate a greater part of the biological and immunological activities which are exhibited by natural lipid A.

(b) Description of the Prior Art

Lipo-polysaccharides are found in the cell-wall of some kinds of gram-negative bacilli as a main component of endotoxin. They exhibit various kinds of biological and immunological activities such as an anti-tumor activity. Lipid A is a lipoid component of lipo-polysaccharides. It is known that the biological and immunological activities is lipo-polysaccharides mostly depend on the lipid A component.

In an attempt to elucidate the chemical structure of lipid A, and to synthesize analogs of sugar moieties of lipid A which exhibit as many biological and immunological properties of natural lipid A as possible, compounds of the following formula have been described by Galanos and Ludritz et al. in 1977 [cf. Int. Rev. Biochem. 14: 239 (1977) and Naturwissensch. 65: 578 (1987)]

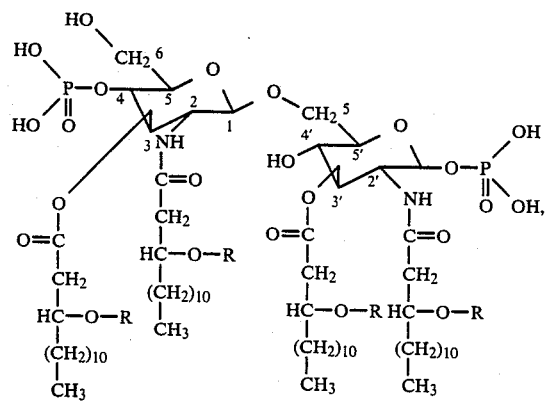

wherein R represents a hydrogen atom or the residue of straight chain aliphatic acid having 12 to 16 carbon atoms, especially myristic acid, that is tetradecanoic acid, represented by a chemical formula of $CH_3(CH_2)_{12}COOH$.

The compounds of the above structure are characterized by two glucosamine groups which are linked together at their 1- and 6'-positions and the amino groups are located at the 2- and 2'-positions and the hydroxy groups are located at the 3- and 3'-positions of the glucosamine groups. Moreover, 3-hydroxy-myristic acid residue are attached by an amide or an ester linkage and the phosphoric acid groups are linked to the 1- and 4'-positions, respectively of the glucosamine groups. The compounds thus simultaneously have both hydrophilic and lipophilic substituents on the glucosamine groups.

In the above chemical formula, the left-handed glucosamine group is called the nonreducing subunit.

On the assumption that it is the nonreducing subunit where the biological and immunological activities of lipid A are mainly concentrated, the inventors have carried out extensive research to synthsize analogs of the nonreducing sugar subunit of lipid A and the thus synthesized products have successively been subjected to a primary biological experiment for screening out, then have achieved the present invention.

SUMMARY OF THE INVENTION

Of the large number of the nonreducing sugar moiety of lipid A which have been synthesized by the inventors, the compounds represented by a following general formula [I] have been identified to have definite biological and immunological activities, for example, inducing interferon- and tumor-necrosis factors and so on:

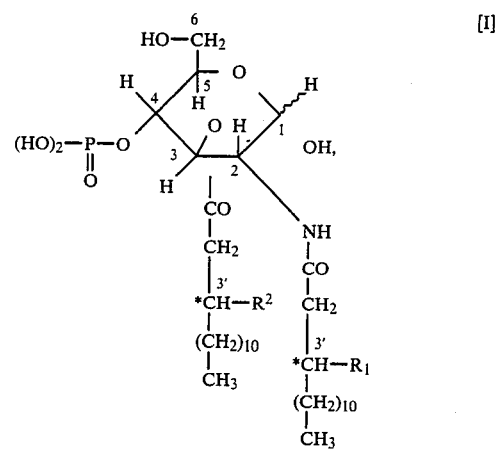

wherein $R_1$ and $R_2$ signify following radicals which will be shown in the next table:

TABLE

| Compound No. | $R_1$ | $R_2$ |
|---|---|---|
| I(R,R) | $-O-CO-(CH_2)_{12}-CH_3$ | $-O-CO-(CH_2)_{12}-CH_3$ |
| II | $-O-CO-(CH_2)_{12}-CH_3$ | $-OH$ |
| II(R,R) | $-O-CO-(CH_2)_{12}-CH_3$ | $-OH$ |
| II(S,S) | $-O-CO-(CH_2)_{12}-CH_3$ | $-OH$ |
| III | $-OH$ | $-O-CO-(CH_2)_{12}-CH_3$ |
| III(R,R) | $-OH$ | $-O-CO-(CH_2)_{12}-CH_3$ |
| III(S,S) | $-OH$ | $-O-CO-(CH_2)_{12}-CH_3$ |
| IV(R) | $-H$ | $-O-CO-(CH_2)_{12}-CH_3$ |

In the foregoing chemical formula and table, the carbon atoms which are marked with an asterisk * indicate as assymetric carbon atom, and there can form a rectus configuration, hereinafter referred to as (R), or a sinister configuration, hereinafter referred to as (S), around those two assymetric carbon atoms.

Briefly explaining the preparing process of this invention, introduction of a 3'-O-(Substituted or non-substituted)-tetradecanoyl radical into the amino group on the C-2 position of a glucopyranose ring is carried out in the presence of dicyclohexylcarbodiimide (DCC) and introduction of the same into the hydroxy group on the C-3 position is carried out in the presence of DCC or dimethylaminopyridine (DMAP). Moreover, following reactions are carried out that protection of the hydroxyl groups on the C-4 and C-6 positions of the glucopyranose ring by coupling them with an isopropylidene group and removal thereof, protection of a hydroxyl group on the C-6 postion with a trityl group and removal thereof, and introduction of a diphenylphosphono group into the hydroxyl group on the C-4 position and removal of the diphenyl group therefrom.

They were the inventors who at first successfully applied above these chemical reactions by properly combining them in a suitable order and manner, to the preparation of analogs of non-reducing monosaccharide moiety of lipid A.

Examples

EXAMPLE 1

Preparation of 2-Deoxy-4-O-phosphono-2-[(3'R)-3'-tetradecanoyloxytetradecanamido]-3-O-[(3'R)-3'-tetradecanoyloxytetradecanoyl]-D-glucose; [Compound No. I (R,R)]

[Step a] Preparation of Benzyl 2-deoxy-4,6-O-isopropylidene-2-[(3'R)-3'-tetradecanoyloxytetradecanamido]-β-D-glucopyranoside; [Introduction of a (3R)-tetradecanoyloxytetradecanoyl group into the C-2 amino group]

Two grams of the known compound benzyl 2-amino-2-deoxy-4,6-O-isopropylidene-β-D-glucopyranoside, of which preparation was published in Agric. Biol. Chem., 48, pages 251–252 (1984) by some of the inventors et al., were dissolved in anhydrous dichloromethane (20 ml), into which (3R)-3-tetradecanoyloxytetradecanoic acid (3 g) and DCC (2.7 g) were added and the mixture was stirred for 4.5 hours at a room temperature and the thus produced DCC-urea was removed by filtration. The remaining solution was washed well with dichloromethane and the filtrate and the washings were combined and was concentrated in vacuo. The thus obtained syrups were subjected to column chromatography (Wako gel C-200) and the effluents obtained from a mixed solvent of dichloromethane and methanol (400:1) were lyophilized from 1,4-dioxane, then the titled compound (2.2 g, 91%) was obtained.

Melting Point: 66°–70° C. $[\alpha]_D - 49.3°$ (C=1.127, chloroform).

Analysis (%) for $C_{44}H_{75}NO_8 = 746.05$. Calcd.: C, 70.83; H, 10.13; N, 1.88. Found: C, 70.68; H, 9.99; N, 1.82.

[Step b] Preparation of Benzyl 2-deoxy-4,6-O-isopropylidene-2-[(3'R)-3'-tetradecanoyloxytetradecanamide]-3-O-[(3'R)-3'-tetradecanoyloxytetradecanoyl]-β-D-glucopyranoside; [Introduction of a (3R)-tetradecanoyloxytetradecanoyl group into the C-3 hydroxy group]

The product of the preceding step (1.35 g) was dissolved in anhydrous dichloromethane (9 ml), to which (3R)-tetradecanoyloxytetradecanoic acid (0.82 g), DCC (0.75 g) and DMAP (0.105 g) were added and the mixture was stirred at a room temperature. After a completion of the reaction was confirmed by means of a thin layer chromatography (ethyl acetate:hexane=1:1), the resultant ureas were removed by filtration and the remaining solution was well washed with dichloromethane and the filtrate and washings were combined and was concentrated in vacuo. The thus obtained syrups were subjected to column chromatography (Wako gel C-200 ) and the effluents obtained from a mixed solvent of hexane and ethyl acetate (10:1) were lyophilized from 1,4-dioxane, then the titled compound (1.73 g, 81%) was obtained.

Melting Point: 64°–65° C. $[\alpha]_D - 23.1°$ (C=0.955, chloroform).

Analysis (%) for $C_{72}H_{127}NO_{11} = 1182.74$. Calcd.: C, 73.11; H, 10.82; N, 1.18. Found: C, 73.38; H, 11.00; N, 1.24.

[Step c] Preparation of Benzyl 2-deoxy-2-[(3'R)-3'-tetradecanoyloxytetradecanamido]-3-O-[(3'R)-3'-tetradecanoyloxytetradecanoyl]-β-D-glucopyranoside [Removal of the isopropylidene group]

The product of the preceding step (1.36 g) was dissolved in 80% acetic acid (20 ml) and the mixture was stirred for 3 hours at 45° C. The reactant was concentrated in vacuo and the residual was subjected to column chromatography (Wako gel C-200) and the titled compound (1.05 g, 80%) was obtained from the mixed solvent of dichloromethane and methanol (100:1).

Melting Point: 101°–101.5° C. $[\alpha]_D - 16.8°$ (C=0.92, chloroform).

$IR\nu_{max}^{nujol} cm^{-1} = 3600-3200$ (OH, NH), 1730 (ester), 1660, 1550 (amido), 760–690 (ph).

[Step d] Preparation of Benzyl 2-deoxy-2-[(3'R)-3'-tetradecanoyloxytetradecanamido]-3-O-[(3'R)-3'-tetradecanoyloxytetradenoyl]-6-O-trityl-β-D-glucopyranoside [Tritylation of the C-6 hydroxyl group]

The product of the preceding step (0.87 g) was dissolved in pyridine (10 ml) and was stirred for 3.5 hours at 90° C. and the resultant residue was dissolved in chloroform. The solution was washed with 2N hydrochloric acid, then with water and was concentrated in vacuo. The thus obtained syrups were subjected to a column chromatography (Wako gel C-200) and the effluents obtained from a mixed solvent of dichloromethane and methanol (500:1) were lyophilized from 1,4-dioxane, then the titled compound (1.01 g, 95%) was obtained.

Melting Point: 93°–97° C. $[\alpha]_D - 19.4°$ (C=1.322, chloroform)

[Step e] Preparation of Benzyl 2-deoxy-4-O-diphenylphosphono-2-[(3'R)-3'-tetradecanoyloxytetradecanamido]-3-O-[(3'R)-3'-tetradecanoyloxytetradecanoyl]-β-D-glucopyranoside [Introduction of a diphenylphosphono group into the C-4 hydroxyl group and removal of the C-6 trityl group]

The product of the preceding step (0.6 g) was dissolved in a mixed solvent (3 ml) of anhydrous dichloromethane and pyridine (2:1), to which DMAP (0.01 g) and diphenylphosphoric acid (0.4 g) were added and the mixture was stirred overnight at room temperature. The reactant was added in chloroform and the mixture was washed with 2N hydrochloric acid, then with water and was dried on sodium sulfate and concentrated in vacuo. The obtained syrups were subjected to column chromatography (Wako gel C-200) and the effluents obtained from dichloromethane were dissolved in acetone (30 ml). $HBF_4$ (0.03 g) was added to the mixture and was stirred for one hour at room temperature, and the reactant was neutralized with triethylamine and was concentrated in vacuo. The thus obtained syrups were subjected to column chromatography (Wako gel C-200) and the effluents obtained from a mixed solvent of dichloromethane and methanol were lyophilized from 1,4-dioxane and the titled compound (0.426 g, 71%) was obtained.

Melting Point: 92°–93° C. $[\alpha]_D - 17.5°$ (C=1.10, chloroform).

NMR data (CDCl$_3$)δ: 3.08 (very broad t, 1H, OH), 3.48 (~d, 1H, $J_{4,5}$~10 Hz, H-5), 3.5–3.8 (m, 3H, H-2, H-6), 4.72 (q, 1H, $J_{3,4} = J_{4,5} = J_{4p}$, 9–10 Hz, H-4), 5.50 (d, 1H, $J_{1,2}$, 8.4 Hz, H-1), 5.56 (dd, 1H, $J_{2,3} \sim 10.3$, $J_{3,4}$, 9.2 Hz, H-3), 7.1–7.4 (m, 15H, ph).

[Step f] Preparation of 2-Deoxy-4-O-diphenylphosphono-2-[(3'R)-3'-tetradecanoyloxytetradecanamido]-3-O-[(3'R)-3'-tetradecanoyloxytetradecanoyl]-D-glucose [Removal of the C-1 benzyl group]

The product of the preceding step (0.11 g) was dissolved in methanol (20 ml), to which Pd-black (0.05 g), which had been in advance subject to a preparatory reduction, was added and the mixture was stirred over a night under streams of hydrogen gas at a room temperature. After removing the remaining catalysts by filtration, the filtrate was washed well with methanol, and the filtrate and washings were combined and they were concentrated in vacuo. The obtained syrups were subject to column chromatography (Wako gel C-200) and the titled compound (0.1 g) was quantitatively obtained from the effluents obtained from a mixed solvent of dichloromethane and methanol (100:1).

Melting Point: 68°–70° C. $[\alpha]_D + 4.2°$ (C=0.622. chloroform).

IR$\nu_{max}^{film}$cm$^{-1}$=3600–3150 (OH, NH), 1740 (ester), 1660, 1540 (amide), 960 (P-O-ph), 800–670 (ph).

NMR data (CDCl$_3$), $\alpha:\beta$=Ca. 2:1δ:0.75–0.95 (m, 12H, Me), 1.0–1.7 (m, 84H, CH$_2$), 2.1–2.5 (m, 8H, COCH$_2$), 4.65–4.83 (2q, 1H, H-4$\alpha,\beta$), 5.26 ($\beta$), 5.46 ($\alpha$) (2dd, 1H, H-3$\alpha,\beta$), 5.33 (d, 2/3H, H-1$\alpha$), 6.29, 6.83 (2d, 1H, $J_{8,1}$, 6.2 Hz, NH$_{\alpha,\beta}$), 7.05–7.4 (m, 10H, ph).

[Step g] The objective compound of Example 1 [Removal of the diphenyl group from the C-4 diphenylphosphono group]

The product of the preceding step (0.06 g) was dissolved in a mixture (50 ml) of methanol and ethanol (1:1), to which Platinum oxide (0.01 g), which had been in advance subject to a preparatory reduction, was added and the mixture was stirred overnight at room temperature under streams of hydrogen gas. After removing the remaining catalysts by filtration, the reactant was well washed with a mixed solution of chloroform and methanol (1:1), and the filtrate and washings were combined and they were concentrated in vacuo. The thus produced material was lyophilized from 1,4-dioxane, then the objective compound (0.52 g) was quantitatively obtained.

Melting Point: 152°–153° C.

$[\alpha]_D + 14°$ (C=0.52, chloroform:methanol=3:1).

IR $^{KBr}$cm$^{-1}$=3680–2500 (OH, NH, CH), 1740 (ester), 1600, 1560 (amide).

Analysis (%) for C$_{62}$H$_{118}$NO$_{14}$P=1132.55. Calcd.: C, 65.75; H, 10.50; N, 1.24. Found: C, 65.39; H, 10.67; N, 1.18.

2-Deoxy-4-O-phosphono-2-(3'-tetradecanoyloxytetradecanmido)-3-O-(3'-tetradecanoyloxytetradecanoyl)-D-glucose was also prepared by the inventors in the same manner as in Example 1 except for introducing into the C-2 amino and C-3 -hydroxyl groups respectively a 3-tetradecanoyloxytetradecanoyl group (neither a rectus nor a sinister type) and the compound was identified by following physico-chemical constants: $[\alpha]_D + 11°$ (C=0.14, chloroform:methanol=3:1).

EXAMPLE 2

Preparation of 2-Deoxy-4-O-phosphoryl-2-[(3'R)- or (3'S)-3'-tetradecanoyloxytetradecanamido]-3-O-[(3'R)- or (3'S)-3'-hydroxytetradecanoyl]-D-glucose [Compound No. II (RR) or (SS)]

[Step a] Preparation of (3R)- or (3S)-(benzyloxymethoxy)-tetradecanoic acid [A material compound of the side chain to be introduced into the C-3 hydroxy group]

Resepectively 2.3 g of (R)- or (S)-3-hydroxytetradecanoic acid acetophenone ester represented by the next chemical formula;

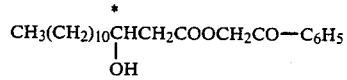

(*: an assymetric carbon atom)

, this compound is commercially available, was dissolved in a mixture (18.4 ml) of dichloromethane and diisopropylethylamine (1:1), to which benzyloxymethylchloride [=C$_6$H$_5$—CH$_2$OCH$_2$Cl, 3.71 ml] was added under cooling with ice, then was stirred at a room temperature. After completion of the reaction was confirmed by means of thin layer chromatography (dichloromethane:methanol=150:1), methanol was added to the reaction mixture, then concentrated in vacuo. The resultant residue was dissolved in chloroform and washed with 2N hydrochloride acid and water, dried and was concentrated in vacuo. The resultant syrups were subjected to column chromatography (Wako gel C-300) and the material (a R type or a S type) respectively effluded from a mixed solvent of hexane and ethyl acetate (15:1) was dissolved in acetic acid (20 ml), to which zinc powder (4.3 g) was added and they were stirred over a night at 50° C. The zinc powder was removed by filtration and washed with dichloromethane. The filtrate and washings were combined and concentrated in vacuo. The obtained syrups were subjected to column chromatography (Wako gel C-300) and the effluent material from dichloromethane or a mixed solvent of hexane and ethyl acetate (10:1) was lyophilized from 1,4-dioxane, then the titled (3R)- or (3S)-compounds were separately obtained (commonly, 2.2 g, 95%).

(R)-Compound: Syrups. $[\alpha]_D - 6.7°$ (C=0.924, chloroform).

Analysis (%) for C$_{22}$H$_{36}$O$_4$=364.51. Calcd.: C, 72.49; H, 9.96. Found: C, 72.30; H, 10.12.

(S)-Compound: Syrups. $[\alpha]_D + 4.0°$ (C=1.34, chloroform).

Analysis (%) for C$_{22}$H$_{36}$O$_4$. Calcd.: C, 72.49; H, 9.96. Found: C, 72.36; H, 9.89.

[Step b] Preparation of (3R)- or (3S)-3-tetradecanoyloxytetradecanoic acid [the compound to be introduced into the C-2 amino group]

The same (3R)- or (3S)-starting compounds as the preceding step (commonly, 2.5 g) were separately dissolved in pyridine (27 ml), to which tetradecanoic chloride (=myristoyl chloride, 2.05 g) and a very small quantity of DMAP were added and were stirred overnight at room temperature. The produced material was dissolved in acetic acid (20 ml) and zinc powder (4.3 g) was added thereto and they were stirred over a night, then the zinc powder was removed by filtration and was well washed with dichloromethane. The filtrate and washings were combined and were concentrated in vacuo. The thus occurred syrups were subjected to column chromatography (Wako gel C-300), then the effluent material from a mixed solvent of hexane and ethyl acetate (10:1) was lyophilized from 1,4-dioxane, and the titled (3R)- or (3S)-compounds were separately obtained (commonly, 2.7 g, 86%).

(R)-Compound: Melting Point 38.5°–40° C. $[\alpha]_D -0.93°$ (C=1.40, chloroform).

Analysis (%) for $C_{28}H_{54}O_4 = 454.71$. Calcd.: C, 73.95; H, 11.97. Found: C, 73.84; H, 12.00.

(S)-Compound: $[\alpha]_D +0.56°$ (C=0.924, chloroform).

Analysis (%) for $C_{28}H_{54}O_4$. Calcd.: C, 73.95; H, 11.97. Found: C, 74.15; H, 11.88.

[Step c] Preparation of Benzyl 2-deoxy-4,6-O-isopropylidene-2-[(3'R)- (3'S)-3'-tetradecanoyloxytetradecanamido]-β-D-glucopyranoside [Introduction of the product of the preceding Step b into the C-2 amino group]

Treated as the same manner as in [Step a of Example 1] employing, as a starting material, the products (3 g) of the preceding Step, the titled compounds (2.2 g, 91%, 2.1 g, 89%) were obtained.

(R)-Compound: Melting Point 66°–70° C. $[\alpha]_D -49.3°$ (C=1.127, chloroform).

Analysis (%) for $C_{44}H_{75}NO_8 = 746.05$. Calcd.: C, 70.83; H, 10.13; N, 1.88. Found: C, 70.68; H, 9.99; N, 1.82.

(S)-Compound: Melting Point 79°–82° C. $[\alpha]_D = 44.9°$ (C=1.20, chloroform.

Analysis (%) for $C_{44}H_{75}NO_8$. Calcd.: C, 70.83; H, 10.13; N, 1.88. Found: C, 70.60; H, 10.23; N, 1.78.

[Step d] Preparation of Benzyl 3-O-[(3'R)- or (3'S)-3'-(benzyloxymethoxy)-tetradecanoyl]-2-deoxy-4,6-O-isopropylidene-2-[(3'R)- (3'S)-3'-tetradecanoyloxytetradecanamido]-β-D-glucopyranoside [Introduction of the product of the foregoing Step a into the C-3 hydroxyl group]

The product (0.75 g) of the preceding Step was dissolved in anhydrous dichloromethane (5 ml), to which the product (0.37 g) of the foregoing Step b, DCC (0.5 g) and DMAP (0.08 g) were added and they were stirred at room temperature. After confirming a completion of the reaction by means of a thin layer chromatography (ethyl acetate:hexane=1:1), the thus produced ureas were removed by filtration and were washed with dichloromethane. The filtrate and washings were combined and were concentrated in vacuo and the thus obtained syrups were subjected to column chromatography (Wako gel C-200). The effluents obtained with a mixed solvent of hexane and ethyl acetate (10:1) were lyophilized from 1,4-dioxane, then the titled (3'RR)- or (3'SS)-compounds were separately obtained (commonly, 1.08 g, 100%).

(3'RR)-Compound: Melting Point 71°–72° C. $[\alpha]_D -22°$ (C=0.91, chloroform).

Analysis (%) for $C_{66}H_{109}NO_{11} = 1092.54$. Calcd.: C, 72.55; H, 10.06; N, 1.28. Found: C, 72.76; H, 10.20; N, 1.31.

(3'SS)-Compound: Melting Point 38°–40° C. $[\alpha]_D -32.1°$ (C=1.126, chloroform).

Analysis (%) for $C_{66}H_{109}NO_{11}$. Calcd.: C, 72.55; H, 10.06; N, 1.28. Found: C, 72.80; H, 10.31; N, 1.30.

[Step e] Preparation of Benzyl 3-O-[(3'R)- or (3'S)-3'-(benzyloxymethoxy)-tetradecanoyl]-2-deoxy-2-[(3'R)- or (3'S)-3'-tetradecanoyloxytetradecanamido]-β-D-glucopyranosid [Removal of the isopropylidene group]

Treated in the same manner as in [Step c of Example 1] employing, as a staring material, the (3'RR)- or (3'SS)-products (0.87 g, 0.8 g, respectively) of the preceding Step, the titled compounds were separately obtained (0.73 g, 87%; 0.66 g, 85%).

(3'RR)-Compound: Melting Point 100°–101.5° C. $[\alpha]_D -35.9°$ (C=0.754, chloroform).

(3'SS)-Compound: Melting Point 94°–96° C. $[\alpha]_D -14°$ (C=1.213, chloroform).

[Step f] Preparation of Benzyl 3-O-[(3'R)- or (3'S)-3'-(benzyloxymethoxy)-tetradecanoyl]-2-deoxy-2-[(3'R)- or (3'S)-3'-tetradecanoyloxytetradecanamido]-6-O-trityl-β-D-glucopyranoside [Introduction of a trityl group into the C-6 hydroxyl group]

Treated as the same manners as in [Step d of Example 1] employing, as a starting material, the (3'RR)- or (3'SS)-products (0.68 g, 0.7 g, respectively) of the preceding Step, the titled compounds were separately obtained (0.78 g, 93%; 0.77 g, 90%).

(3'RR)-Compound: $[\alpha]_D -31.2°$ (C=0.902, chloroform).

(3'SS)-Compound: Melting Point 70°–72° C. $[\alpha]_D -17°$ (C=0.87, chloroform).

[Step g] Preparation of Benzyl 3-O-[(3'R)- or (3'S)-3'-(benzyloxymethoxy)-tetradecanoyl]-2-deoxy-4-O-diphenylphosphono-2-[(3'R)- or (3'S)-3'-tetradecanoyloxytetradecanamido]-β-D-glucopyranoside [Introduction of a diphenylphosphono group into the C-4 hydroxyl group and removal of the C-6 trityl group]

Treated in the same manner as in [Step e of Example 1] employing, as a starting material, the products (0.55 g, 0.55 g, respectively) of the preceding step, the titled compounds (0.374 g, 68%; 0.363 g, 66%) were separately obtained.

(3'RR)-Compound: Melting Point 69.5°–70.5° C. $[\alpha]_D -14.5°$ (C=0.724, chloroform).

(3'SS)-Compound: Melting Point 67°–70° C. $[\alpha]_D -16.3°$ (C=1.02, chloroform).

[Step h] Preparation of 2-deoxy-4-O-diphenylphosphono-3-O-[(3'R)- or (3'S)-3'-hydroxytetradecanoyl]-2-[(3'R)- or (3'S)-3'-tetradecanoyloxytetradecanamido]-D-glucose [Removal of the C-1 benzyl group and removal of a benzyloxymethyl group from the side chain on the C-3 substituent]

Treated as the same manners as were made in [Step f of Example 1] employing, as a starting material, the products (0.158 g, 0.16 g, respectively) of the predceding step, the titled compounds (0.128 g, 97%; 0.14 g, 100%) were separately obtained.

(3'RR)-Compound: Melting Point 87°–88° C. $[\alpha]_D -2.1°$ (C=1.17, chloroform).

(3'SS)-Compound: Melting Point 64.5°–65° C. $[\alpha]_D +9.5°$ (C=0.786, chloroform).

[Step i] Preparation of the objective compound of Example 2 [Removal of the diphenyl group from the C-4 diphenylphosphono group]

Treated as the same manners as were made in [Step g of Example 1] employing, as a starting material, the products (0.128 g, 0.14 g, respectively) of the preceding Step, the final objective compounds were separately obtained.

(3'RR)-Compound: Melting Point 172°–174° C. $[\alpha]_D +12.8°$ (C=0.97, Chloroform:methanol=3:1).

$IR\nu_{max}^{KBr}cm^{-1} = 3680-2500$ (OH, NH, CH), 1740, 1720 (ester), 1645, 1650 (amide).

Analysis (%) for $C_{48}H_{92}NO_{13}P=922.21$. Calcd.: C, 62.51; H, 10.06; N, 1.52. Found: C, 62.85; H, 9.93; N, 1.60.

(3'SS)-Compound: Melting Point 156°–158° C. $[\alpha]_D+17.2°$ (C=0.571, chloroform:methanol=3:1).

$IR\nu^{KBr}cm^{-1}=3680-2500$ (OH, NH, CH), 1740, 1720 ester), 1655, 1550 (amide).

Analysis (%) for $C_{48}H_{92}NO_{13}P$. Calcd.: C, 62.51; H, 10.06; N, 1.52. Found: C, 62.30; H, 10.26; N, 1.35.

2-Deoxy-3-O-(3'-hydroxytetradecanoyl)-4-O-phosphoryl-2-(3'-tetradecanoyloxytetradenamido)-D-glucose was also prepared in the same manner as carried out through the steps 'a' to 'i' in Example 2 but employing the materials of neither a rectus type nor a sinister type and the compound exhibits following physico-chemical constants:

$[\alpha]_D+8.76°$ (C=0.616, chloroform).
$IR\nu_{max}^{Nujol}cm^{-1}=3600-3200$ (OH, NH), 1720 (ester), 1640, 1540 (amide).

Analysis (%) for $C_{48}H_{92}NO_{13}P$. Calcd.: C, 62.51; H, 10.06; N, 1.52. Found: C, 62.39; H, 10.23; N, 1.52.

EXAMPLE 3

Preparation of 2-Deoxy-2-[(3'R)- or (3'S)-3'-hydroxytetradecanamido]-3-O-[(3'R)- or (3'S)-3'-tetradecanoyloxytetradecanoyl]-4-O-phosphoryl-D-glucose

[Step a] Preparation of Benzyl 2-[(3'R)- or (3'S)-3'-(benzyloxymethoxy)tetradecanamido]-2-deoxy-4,6-O-isopropylidene-β-D-glucopyranoside [Introduction into C-2 amino group]

Following through to [Step c of Example 2] but employing the product of [Step b of Example 2] for [Step a of Example 2], the titled compounds were obtained.

(3'R)-Compound: Melting Point 109°–110° C., $[\alpha]_D-56.5°$ (C=0.66, chloroform), Yield rate 80.2%.
(3'S)-Compound: Melting Point 67°–70° C., $[\alpha]_D-49.7°$ (C=0.561, chloroform), Yield rate 84%.

[Step b] Preparation of Benzyl 2-[(3'R)- or (3'S)-3'-(benzyloxymethoxy)tetradecanamido]-2-deoxy-4,6-O-isopropylidene-3-O-[(3'R)- or (3'S)-3'-tetradecanoyloxytetradecanoyl]-β-D-glucopyranoside [Introduction into C-3 hydroxyl group]

Following through to [Step d of Example 2] but employing the product of [step a of Example 2] for [Step b of Example 2], the titled compounds were obtained.

(3'RR)-Compound: Melting Point 70°–72° C., $[\alpha]_D-24.6°$ (C=1.21, chloroform), Yield rate 92%.
(3'SS)-Compound: Melting point 39°–40° C., $[\alpha]_D-30.1°$ (C=1.18, chloroform), Yield rate 100%.

[Steps c–g] Preparation of the objective compounds of Example 3

Following to [Steps e–i of Example 2], the product of the preceding Step was subject to following chemical reactions in the sequence of (c) Removal of the C-4, 6-O-isopropylidene group, (d) Introduction of a trityl group into the C-6 OH group, (e) Introduction of a diphenylphosphono group into the C-4 OH group and removal of the C-6 trityl group, (f) Removal of the C-1 benzyl group and the benzyloxymethyl group from the substituent connected with the C-2 amino group and (g) Removal of the diphenyl group from the substituent connected with the C-4 OH group, then the titled compounds were separately obtained.

(3'RR)-Compound: Melting Point 157°–159° C., $[\alpha]_D+13.7°$ (C=0.512, chloroform:methanol=3:1).

$IR\nu_{max}^{KBr}cm^{-1}=3680-2500$ (OH, NH, CH), 1735, 1720 ester), 1640, 1560 (amide).

(3'SS)-Compound: Melting Point 154°–155° C., $[\alpha]_D+18.4°$ (C=0.896, chloroform:methanol=3:1).

2-Deoxy-2-(3'-hydroxytetradecanamido)-3-O-(3'-tetradecanoyloxytetradecanoyl)-4-O-phosphoryl-D-glucose was also prepared following to the Steps from 'a' to 'g' of Example 3 but employing the materials neither a rectus nor a sinister type and this compound exhibits following physico-chemical constants:

$[\alpha]_D+7.69°$ (C=0.442, chloroform).
$IR\nu_{max}^{Nujol}cm^{-1}=3600-3100$ (OH, NH), 1720 (ester), 1630, 1540 (amide).

Analysis (%) for $C_{48}H_{92}NO_{13}=922.21$. Calcd.: C, 62.51; H, 10.05; N, 1.52. Found: C, 62.44; H, 10.18; N, 1.50.

EXAMPLE 4

Preparation of 2-Deoxy-4-O-phosphoryl-2-tetradecanamido-3-O-[(3'R)-3'-tetradecanoyloxytetradexanoyl]-D-glycopyranose

[Step a] Preparation of Benzyl 2-deoxy-4,6-O-isopropylidene-2-tetradecanamido-β-D-glucopyranoside [Introduction of a tetradecanoyl group into C-2 amino group]

Following to [Step a of Example 1] but employing tetradecanoic acid for (3'R)-3'-tetradecanoyloxytetradecanoic acid, the titled compound was obtained in a yield rate of 88.5%.

[Step b] Preparation of Benzyl 2-deoxy-2-tetradecanamido-3-O-[(3'R)-3'-tetradecanoyloxytetradecanoyl]-β-D-glucopyranoside [Introduction of a (3R)-3-tetradecanoyloxytetradecanoyl group into the C-3 OH group and removal of the 4,6-O-isopropylidene group]

The product (800 mg) of the preceding Step was dissolved in dichloromethane (8 ml), to which (3R)-3-tetradecanoyloxytetradecanoic acid (700 mg), DMAP (95 mg) and DCC (400 mg) were added and they were left for 8 hours at a room temperature. After confirming completion of the reaction by means of a thin layer chromatography, the thus occurred ureas were removed by filtration and the filtrate was concentrated in vacuo. The thus obtained product dissolved in a mixture of 90% acetic acid, dichloromethane and methanol and they were stirred at 50° C. After confirming a completion of the reaction, the reactant was concentrated in vacuo and the residue was subjected to column chromatography (Wako gel C-300) and employing as a solvent for eluting (a) dichloromethane and (b) a mixed solvent of dichloromethane and methanol (250:1), the titled compound (480 mg, 49%) was obtained from the solvent (b).

$[\alpha]_D-21.48°$ (C=3.453, chloroform).

[Steps c–f] Preparation of the objective compound of Example 4

Following to [Steps d–g of Example 1], the product of the preceding Step was subject in turn to chemical reactions of (c) Tritylation of the C-6 OH group, (d) Diphenylphosphorylation of the C-4 OH groups and removal of the trityl group, (e) Removal of the C-1 benzyl group and (f) Removal of the diphenyl group from the substituent connected to the C-4 OH group, there was obtained the titled objective compound.

Melting Point 150°–151° C.

IR$\nu_{max}^{KBr}$cm$^{-1}$=3450 (OH, NH), 2960, 2870 (CH$_2$, CH$_3$), 1740 (ester), 1650, 1560 (amide).

The study of stereoisomer teaches that a rectus configuration and a sinister configuration, which are formed around one assymetric carbon atom as a center, stand in diastereomer relationship with each other, which is not identical with an optical antipode relation between a dextro and a levo types. So, as can be seen in the examples of this specification, a mother compound and its rectus and sinister compounds exhibit different physico-chemical properties such as a melting point, an angle of optical rotation and solubility, consequently, exhibit different biological and immunological activities with respect to each other.

This is why the inventors are investigating for stereoisomers of some derivatives of the nonreducing monosaccharide subunit of lipid A which have thus far been synthesized and have been identified to have certain interesting biological and immunological properties by them.

More concretely, the compounds of this invention are expected to exhibit definite effects for proclotting the enzyme of horseshoe crab, inducing interferon- and tumor-necrosis factors, furthermore, they act as mitogens for polyclonal B cells and as adjuvants.

What we claim is:
1. 2-Deoxy-4-O-phosphono-2-[(3'R)-3'-tetradecanoyloxytetradecanamido]-3-O-[(3'R)-3'-tetradecanoyloxytetradecanoyl]-D-glucose.
2. 2-Deoxy-4-O-phosphono-2-(3'-tetradecanoyloxytetradecanamido]-3-O-(3'-hydroxytetradecanoyl)-D-glucose.
3. 2-Deoxy-4-O-phosphono-2-[(3'R)-3'-tetradecanoyloxytetradecanamido]-3-O-[(3'R)-3'-hydroxytetradecanoyl]-D-glucose.
4. 2-Deoxy-4-O-phosphono-2-[(3'S)-3'-tetradecanoyloxytetradecanamido]-3-O-[(3'S)-3'-hydroxytetradecanoyl]-D-glucose.
5. 2-Deoxy-4-O-phosphone-2-(3'-hydroxytetradecanamido)-3-O-(3'-tetradecanoyloxytetradecanoyl)-D-glucose.
6. 2-Deoxy-4-O-phosphono-2-[(3'R)-3'-hydroxytetradecanamido]-3-O-[(3'R)-3'-tetradecanoyloxytetradecanoyl]-D-glucose.
7. 2-Deoxy-4-O-phosphono-2-[(3'S)-3'-hydroxytetradecanamido]-3-O-[(3'-tetradecanoyloxytetradecanoyl]-D-glucose.
8. 2-Deoxy-4-O-phosphono-2-tetradecanamido-3-O-[(3'R)-3'-tetradecanoyloxytetradecanoyl]-D-glucose.

* * * * *